US00PP36613P3

(12) United States Plant Patent
Olesen

(10) Patent No.: US PP36,613 P3
(45) Date of Patent: Apr. 22, 2025

(54) ROSE PLANT NAMED 'Poulpah109'

(50) Latin Name: *Rosa hybrida*
Varietal Denomination: Poulpah109

(71) Applicant: Mogens Nyegaard Olesen, Fredensborg (DK)

(72) Inventor: Mogens Nyegaard Olesen, Fredensborg (DK)

(73) Assignee: POULSEN ROSER A/S, Fredensborg (DK)

( * ) Notice: Subject to any disclaimer, the term of this patent is extended or adjusted under 35 U.S.C. 154(b) by 13 days.

(21) Appl. No.: 18/831,192

(22) Filed: Sep. 5, 2024

(65) Prior Publication Data

US 2025/0107463 P1 Mar. 27, 2025

(30) Foreign Application Priority Data

Sep. 22, 2023 (QZ) ..... PBR 20231977

(51) Int. Cl.
*A01H 5/02* (2018.01)
*A01H 6/74* (2018.01)

(52) U.S. Cl.
USPC ..... Plt./119

(58) Field of Classification Search
USPC ..... Plt./101, 102, 116, 119, 122
See application file for complete search history.

*Primary Examiner* — Susan McCormick Ewoldt
*Assistant Examiner* — Zachariah Allan Kay

(57) ABSTRACT

A new garden rose plant of the miniature class which has abundant, red orange flowers and attractive foliage. This new and distinct variety has shown to be uniform and stable in the resulting generations from asexual propagation.

2 Drawing Sheets

Botanical designation: *Rosa hybrida.*
Variety denomination: 'Poulpah109'.

This application claims priority to Plant Breeder's Rights Application Number 2023/1977, which was filed at the Community Plant Variety Rights Office in the European Union on Sep. 22, 2023, the contents of which are hereby incorporated by reference for all purposes.

SUMMARY OF THE INVENTION

The present invention constitutes a new and distinct variety of rose plant which originated from a controlled crossing between the female seed parent, an unnamed seedling, and the male pollen parent, also an unnamed seedling. Both of the parent varieties are non-patented.

The two parents were crossed during the summer of 2016 and the resulting seeds were planted in a controlled environment in Fredensborg, Denmark. The new variety, named 'Poulpah109', originated as a single seedling from the stated cross.

The new variety may be distinguished from its male pollen parent and female seed parent primarily by the following characteristics. The male pollen parent plant has orange flowers while the new variety has red orange flowers. The female seed parent plant has russet brown flowers while the new variety has red orange flowers.

The objective of the hybridization of this rose variety was to create a new and distinct variety with unique qualities, such as:

1. Uniform and abundant red orange flowers;
2. Vigorous, but compact growth when propagated on its own roots;
3. Exceptional disease resistance.

This combination of qualities is not present in previously available commercial cultivars of this type, known to the inventor, and distinguish 'Poulpah109' from all other varieties of which we are aware.

As part of the rose development program, Mogens N. Olesen germinated the seeds from the aforementioned hybridization during winter of 2016 and conducted evaluations on the resulting seedlings in a controlled environment in Fredensborg, Denmark. 'Poulpah109' was selected in the spring of 2017 by the inventor as a single plant from the progeny of the aforementioned hybridization.

Asexual reproduction of 'Poulpah109' by rooted cuttings was first done by Mogens N. Olesen in the nursery in Fredensborg, Denmark in July 2017. This initial and other subsequent asexual propagations conducted in controlled environments have demonstrated that the characteristics of 'Poulpah109' are true to type and are transmitted from one generation to the next.

DESCRIPTION OF THE DRAWING

The accompanying color illustrations show as true as is reasonably possible to obtain in color photographs of this type, the typical characteristics of the buds, flowers, leaves, and stems, of 'Poulpah109'.

Specifically illustrated in FIG. 1 of the drawings are open flowers at various stages of development viewed from above, a partially opened flower and mostly closed flower bud viewed from the side, flower petals detached revealing the reproductive flower parts.

Figure 1:
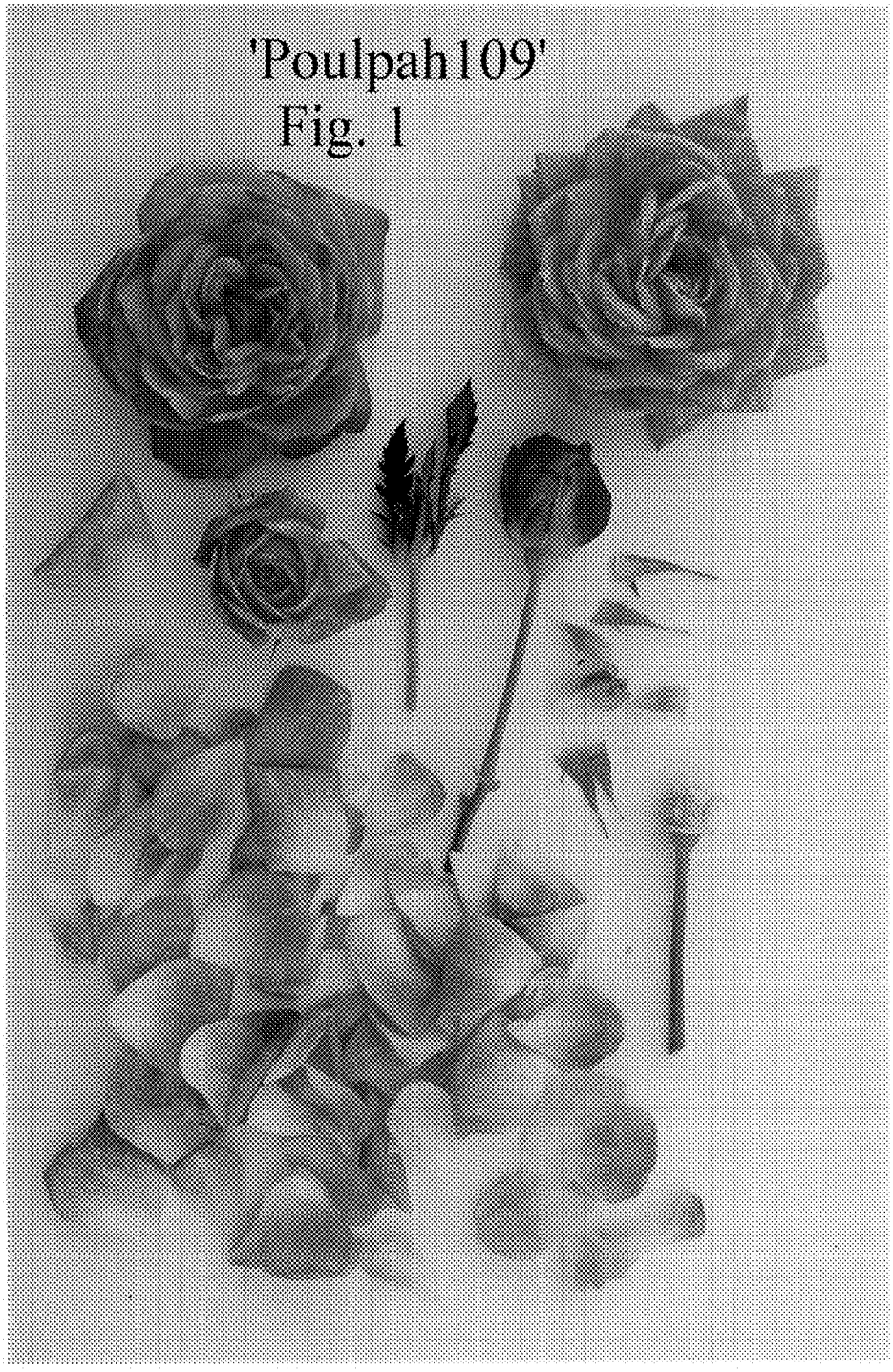
Figure 2:
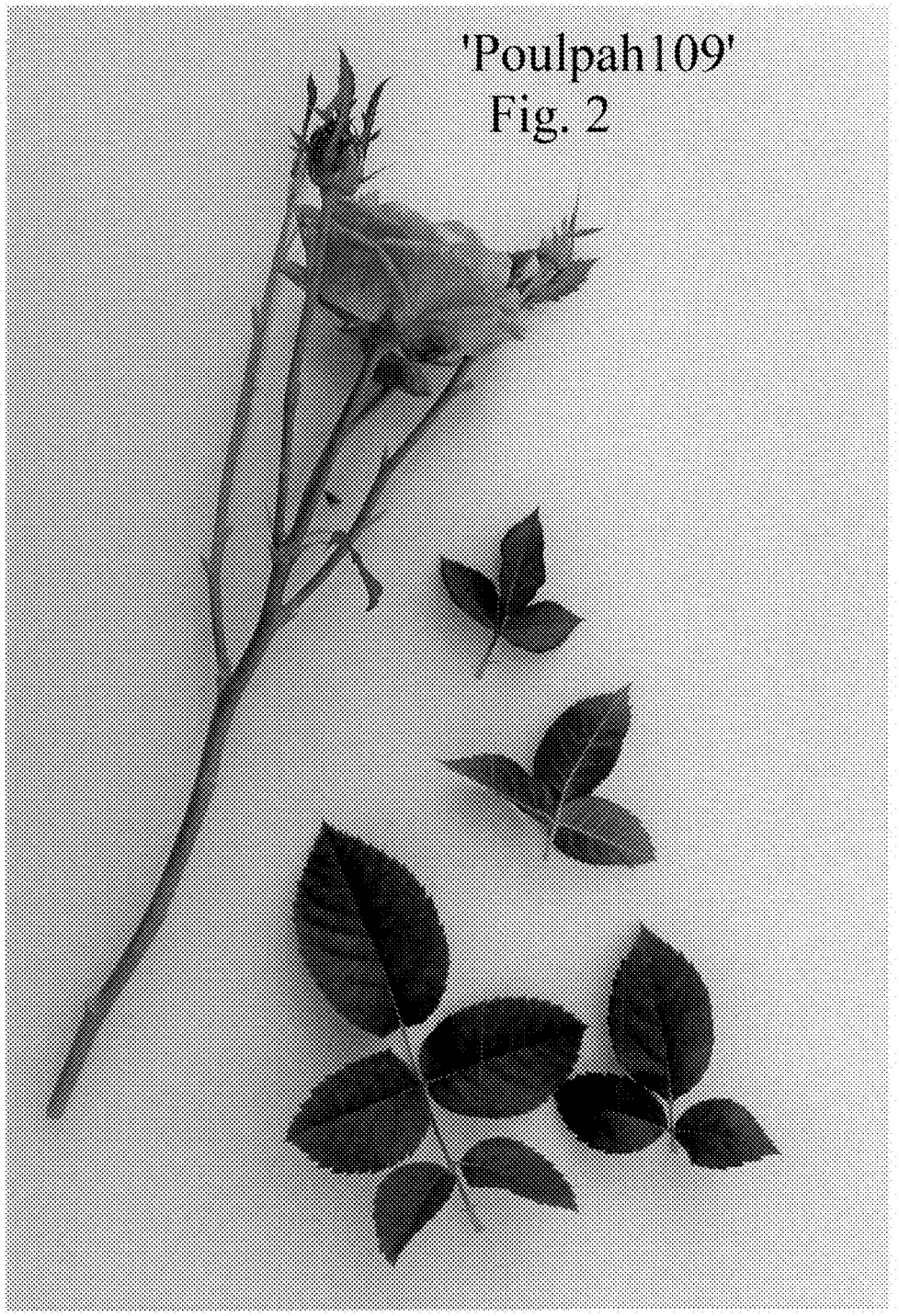

Specifically illustrated in FIG. 2 of the drawings are mature and juvenile leaves showing anthocyanin, and a cluster of flowers and flower buds on a bare stemmed branch. Plants shown are 6 months of age.

DETAILED DESCRIPTION OF THE VARIETY

The following is a description of 'Poulpah109', as observed in its growth in a glass house located in Odense Denmark. Observed plants are 6 months of age, and were grown on their own roots in 24 cm containers. Color references are made using The Royal Horticultural Society (London, England) Colour Chart, 2001, except where common terms of color are used.

For a comparison, several physical characteristics of the rose variety 'Poulpah110', U.S. Plant Pat. No. 35,194 are now compared to 'Poulpah109'. General tonality of flower color for the comparison variety is Yellow-Orange 23B with intonations of Orange-Red 31A, while the claimed plant is Red Group 41C and Orange-Red Group 32B. The sepal margins of the comparison have weak foliaceous appendages, while sepal margins of the claimed plant have strong foliaceous appendages. The comparison variety flowers have a light floral scent while 'Poulpah109' has an obviously strong perfume.

FLOWER AND FLOWER BUD

Blooming habit: Continuous.

Flower bud:

- *Size*.—Upon opening, 18 mm in length from base of receptacle to end of bud. Bud diameter is 14 mm.
- *Bud form*.—Ovoid.
- *Bud color*.—As sepals divide petals are Greyed-Purple Group 185B.
- *Sepal inner surface*.—Color: Yellow-Green Group 147A. Surface: Lightly pubescent.
- *Sepal outer surface*.—Color: Yellow-Green Group 144A, and Yellow-Green Group 147A. Texture: Smooth.
- *Sepal shape*.—Apex: Cirrhose. Base: Flat at union with receptacle.
- *Sepal margin*.—Margins have strong foliaceous appendages on three of the five sepals.
- *Sepal size*.—25 to 50 mm long, 6 to 15 mm wide.
- *Receptacle*.—Texture: Smooth. Size: 5 mm in height, 7 mm wide. Color: Yellow-Green Group 144A. Shape: Urceolate
- *Pedicel*.—Surface: Smooth. Length: About 52 mm. Diameter: 2 mm on average. Color: Yellow-Green Group 144A. Strength: Strong.
- *Peduncle*.—Length: 20 to 95 mm. Diameter: About 3.5 mm. Color: Yellow-Green Group 144A. Texture: Smooth.

Flower bud development: Flower buds are borne singly and in clusters of 3 flower buds per stem.

Flower bloom:

- *Fragrance*.—Very strong perfume.
- *Duration*.—The blooms have a duration on the plant of approximately 18 days. Petals fall cleanly away from plant after flowers have fully matured.
- *Size*.—Flower diameter is 80 mm when open. Flower depth is 38 mm.
- *Flower shape*.—Quartered-rosette, very double, with many overlapping petals packed into quarter sections.
- *Shape of flower, side view*.—The upper portion is flattened convex. The lower portion is concave.

Petalage: Under normal conditions, flowers have about 71 petals.

General tonality of flower: Open flowers are Red Group 41C and Orange-Red Group 32B. After flowers have been open about one week, the general tonality changes to Red Group 38A and Orange Group 29B.

Petal color:

- *Upon opening, outer petals*.—Upper surface: Large spot of Yellow Group 10B at the petal base. Splashes of Orange-Red Group 33C at the middle and marginal zone. Lower surface: Yellow Group 8C splashed with Red Group 41C at the middle and marginal zone. The basal zone is Yellow Group 4C. Guard petals are marked with Red Group 47B.
- *Upon opening, inner petals*.—Upper surface: Yellow Group 10C at the base with splashes of Orange Group 27A and Orange-Red Group 32A at the middle and marginal zone. Lower surface: Yellow Group 10C at the basal zone, splashed with Red Group 41C at the middle and marginal zone.
- *After opening, outer & inner petals*.—Upper surface: Yellow Group 8B at the base of the petal. Splashed with Red Group 39B. Lower surface: Yellow-Orange Group 18C splashed with Red Group 39B. Yellow Group 4C at the basal zone.

Petals:

- *Petal reflex*.—Bilateral moderate to strong.
- *Margin*.—Entire and uniform. No undulations.
- *Shape*.—Broad and elliptic. Apex shape: Rounded. Base shape: Acute.
- *Size*.—42 mm (l)×37 mm (w).
- *Texture*.—Smooth.
- *Thickness*.—Average.

Petaloids:

- *Size*.—15 mm (l) by 14 mm (w).
- *Quantity*.—About 12.
- *Shape*.—Elliptical with an acute base and rounded. apices.
- *Color*.—Orange-Red Group 32A with basal zone color Yellow Group 10A on the upper surface. The underside is Yellow-Orange Group 18B splashed with Orange-Red Group 33B. The base of the underside is Yellow Group 10A.

Reproductive flower parts:

- *Pollen*.—None observed.
- *Anthers*.—Size: 1 mm in length. Color: Greyed-Orange Group 163D. Quantity: 45 on average.
- *Filaments*.—Color: Yellow Group 12A. Length: 5 mm.
- *Pistils*.—Length: 10 mm. Quantity: 30 on average.
- *Stigmas*.—Color: Green-White Group 157A.
- *Styles*.—Color: Green-White Group 157A.
- *Location of stigmas*.—Superior in location relative to the length of the filaments and the height of the anthers.
- *Hips*.—None Observed.

PLANT

Plant growth: Upright. Plants are about 45 cm in height, and 40 cm wide.

Stems:

- *Color of juvenile growth*.—Yellow-Green Group 144B.
- *Color of mature growth*.—Yellow-Green Group 144A.
- *Length*.—Canes are about 25 to 30 cm from the base of the plant to the flowering portion.
- *Diameter*.—About 5 mm.
- *Internodes*.—On mature canes about 30 to 40 mm between nodes.
- *Surface texture*.—Young wood: Smooth. Older wood: Smooth.

Long prickles:

*Incidence*.—Low, about 2 prickles per 10 cm of stem.

*Size*.—Average length of prickles on mature stems is mm.

*Shape*.—Upper portion is linear. Lower portion is concave.

*Color*.—Juvenile prickles: Yellow-Green Group 144B. Mature prickles: Yellow-Green Group 144B.

Plant foliage:

*Compound leaf*.—About 125 mm (l)×100 (w).

*Quantity*.—3 leaves per 10 cm of stem on average.

*Leaf bearing angle to the stem*.—45 degrees.

*Color of juvenile foliage*.—Upper side: Yellow-Green Group 146B with marginal intonations of Greyed-Purple Group 183B. Lower side: Greyed-Purple Group 183B.

*Color of mature foliage*.—Upper side: Yellow-Green Group 146A. Lower side: Yellow-Green Group 147B.

Plant leaves and leaflets:

*Stipules*.—Size: 11 mm long, 3 mm wide. Quantity: 2 per compound leaf. Shape: Linear, slightly broad based with outward extending apices. Margins: Finely serrated. Color: Yellow-Green Group 144A.

*Petiole*.—Length: 15 mm. Diameter: 2 mm. Upper surface color: Yellow-Green Group 144A. Lower surface color: Yellow-Green Group 144A.

*Rachis*.—Length: About 43 mm. Upper surface color: Yellow-Green Group 144A. Lower surface color: Yellow-Green Group 144A.

*Leaflet*.—Quantity: Normally 5 leaflets. Margins: Serrated. Size: Terminal leaflets are about 63 mm long, 40 mm wide. Shape: Generally elliptical. Base: Rounded. Apex: Acute. Texture: Smooth. Thickness: Average. Arrangement: Odd pinnate. Venation: Reticulate. Glossiness: Not glossy.

Disease resistance: Above average resistance to powdery mildew *Sphaerotheca pannosa* var. *rosae*, downy mildew *Peronospora sparsa*, rust. *Phragmidium* spp., black spot *Diplocarpon rosae*, and *Botrytis cinerea* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

I claim:

1. A new and distinct variety of rose plant named 'Poulpah109' substantially as described and illustrated herein.

* * * * *

'Poulpah109'

'Poulpah109'